(12) United States Patent
Hunt et al.

(10) Patent No.: US 7,344,847 B2
(45) Date of Patent: Mar. 18, 2008

(54) NANOSCALE PATTERNING AND IMMOBILIZATION OF BIO-MOLECULES

(75) Inventors: Alan J. Hunt, Plymouth, MI (US); Lingjie J. Guo, Ann Arbor, MI (US); Jeremy Damon Hoff, Ann Arbor, MI (US); Li-Jing Cheng, Ann Arbor, MI (US); Edgar Meyhofer, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 428 days.

(21) Appl. No.: 11/066,804

(22) Filed: Feb. 25, 2005

(65) Prior Publication Data

US 2006/0194252 A1  Aug. 31, 2006

(51) Int. Cl.
G01N 33/53 (2006.01)
H01C 17/075 (2006.01)
C23C 22/00 (2006.01)

(52) U.S. Cl. ...................... 435/7.5; 435/7.1; 427/98.4; 427/98.8

(58) Field of Classification Search ................ 435/7.1, 435/7.5; 427/98.4, 98.8
See application file for complete search history.

(56) References Cited

U.S. PATENT DOCUMENTS 5,772,905 A  6/1998 Chou
6,265,552 B1  7/2001 Schatz (Continued)

OTHER PUBLICATIONS

Committee on Implications of Emerging Micro- and Nanotechnologies, "Implications on emerging micro- and nanotechnologies," 2002, Air Force Science and Technology Board, Division on Engineering and Physical Sciences, National Research Council of the National Academies, The National Academies Press, Washington, DC.*

(Continued)

*Primary Examiner*—Long V. Le
*Assistant Examiner*—Unsu Jung
(74) *Attorney, Agent, or Firm*—Harness, Dickey & Pierce, P.L.C.

(57) ABSTRACT

A support for immobilizing target molecules comprises a substrate having a plurality of binding regions for binding select target molecules, with target-molecule-capturing agent immobilized at the binding regions. The binding regions are intersperse among other non-binding regions. The binding regions are of sub-micron size, have high selectivity and high binding capacity, and prevent or at least minimize loss of target molecule activity.

10 Claims, 4 Drawing Sheets

U.S. PATENT DOCUMENTS

| | | |
|---|---|---|
| 6,797,393 B2 | 9/2004 | Qiao et al. |
| 6,812,038 B1 | 11/2004 | Mendel-Hartvig et al. |
| 6,815,078 B2 | 11/2004 | Qiao et al. |
| 6,825,032 B2 | 11/2004 | Dapron et al. |
| 2002/0173033 A1* | 11/2002 | Hammerick et al. ..... 435/305.2 |

OTHER PUBLICATIONS

Chou et al., "Nanoimprint lithography," J. Vac. Sci. Techno. B, Nov./Dec. 1996, vol. 14, pp. 4129-4133.*

Pfeiffer et al., "Multistep profiles by mix and match of nanoimprint and UV lithography," Microelectronic Engineering, 2001, vol. 57-58, pp. 381-387.*

Resnick et al., "Release layers for contact and imprint lithography," Semiconductor International, Jun. 2002, vol. 25, pp. 71-80.*

Hoff, J. Damon et al., "Nanoscale Protein Patterning by Imprint Lithography," Nano Letters, vol. 4, No. 5, 2004, pp. 853-857 (published on Web Apr. 13, 2004).

Joglekar, Ajit P. et al., "Optics at critical intensity: Applications to nanomorphing," PNAS, Apr. 20, 2004, vol. 101, No. 16, pp. 5856-5861.

BMES Brochure "2003 Annual Fall Meeting Call for Papers and Program Announcement" and Abstract submitted for Oct. 1-4, 2003 meeting in Nashville, TN.

* cited by examiner

Imprint PMMA file with Si template

Remove PMMA residue with $O_2$ plasma etch

RIE etch oxide; Passivate Si surface

Strip residual PMMA

Covalently bind aminosilane by vapor deposition

Covalently bind biotin

Bind streptavidin

Bind biotinylated target protein

NANOSCALE PATTERNING AND IMMOBILIZATION OF BIO-MOLECULES

GOVERNMENT'S RIGHT CLAUSE

This invention was made with government support provided by the National Science Foundation (Grant No. 0133659) and by DARPA (Grant No. N66001-02-C-8039). The government has certain rights in the invention.

FIELD OF THE INVENTION

The present invention relates to methods and devices for isolating, harvesting, detecting and/or quantifying target molecules, including organic and biologic target material, and particularly proteins.

BACKGROUND OF THE INVENTION

The biological roles of proteins are extraordinarily diverse and include catalysis, force generation, mechanical support, signaling, and sensing. Beyond their central importance to biology, proteins are of great interest because these subcellular nanomachines have potential to be integrated into micro- or nanofabricated devices to create low-cost, robust technologies of unprecedented small scale and high efficiency. Applications include biosensors, actuation of microelectromechanical systems (MEMS), and tissue engineering, as well as screening tools for proteomics and pharmacology, and basic biological research. However, both the study and application of proteins have been challenged by the inherent difficulties associated with positioning these tiny objects. Thus, there is a need for enabling technology to more precisely immobilize biomolecules.

SUMMARY OF THE INVENTION

In one aspect, the invention provides methods and devices to more precisely immobilize molecules, particularly biomolecules in well-defined patterns while retaining their native functionality.

In another aspect, the invention provides binding regions for target molecule capture, such as protein capture; and other regions that essentially block proteins from non-specific surface binding. The non-binding other regions are passivated surfaces and provide a surface resistant to non-specific binding.

Accordingly, the invention provides a substrate with at least one surface or portion thereof having desired functionalities. Thus treated, or modified, the surface is substantially resistant to non-specific binding. Further, the functionalities are capable of interacting specifically with target-molecule-capturing agents with which they come in contact. Thus, the substrate of the invention affords a high degree of specific binding. The invention is illustrated using protein as the target molecule.

In order to immobilize target-molecule-capturing agents and target molecules onto a solid support, the support is preferably modified by certain chemical functional agents. In general, the chemically functional agent is a bi-functional molecule having chemical functionalities that are capable of reacting or interacting with the substrate and with the molecules to be immobilized on the substrate.

In one aspect, once a substrate is modified, target-molecule-capturing agents are placed onto the substrate to generate target molecule microarray content. For example, protein capture agents are molecules which can interact with proteins in high affinity and high specificity.

In general, a protein microarray on a substrate can be prepared by first modifying a solid support, followed by depositing various target-molecule-capturing agents onto the modified substrate at pre-defined locations. Supports of choice for protein microarray applications can be organic, inorganic or biological. Some commonly used support materials include glass, plastics, metals, semiconductors. The support can be transparent or opaque, flexible or rigid. It is preferably transparent. In one aspect, it preferably has surface oxides at desired regions. It is preferred to immobilize the target-molecule-capturing agents onto a substrate through chemical covalent bond.

In one particular aspect, a solid support allows covalent or non-covalent attachment of a protein or a protein capture agent on the surface of the support. The support is selected and prepared to overcome the difficulty that proteins tend to bind to surfaces in a non-specific manner and, in doing so, lose their biological activity. More specifically, the invention support substrates are prepared so as to resist non-specific binding and do not inhibit the activity of specifically bound proteins. Thus, the invention provides support substrates and methods that overcome such difficulties and provide surface functionality that are capable of interacting with protein capture agents, and also resist non-specific protein binding to areas relatively devoid of protein capture agents.

The assay devices of the invention may be prepared and used for isolating, detecting and/or quantitating a variety of target molecules, for example, macromolecules, large proteins, antibodies, glycoproteins, DNA, RNA and polysaccharides. The assay devices of the invention may also be prepared and used to bind molecules such as small organic molecules, drugs, small proteins, peptides, polypeptides, modified polypeptides, oligonucleotides or small polymers and compounds with smaller molecular weights. Selection of appropriate binding region size and target-molecule-capturing agent provides a format that offers selectivity and high binding capacity.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF THE PREFERRED EMBODIMENTS

Figure 1:
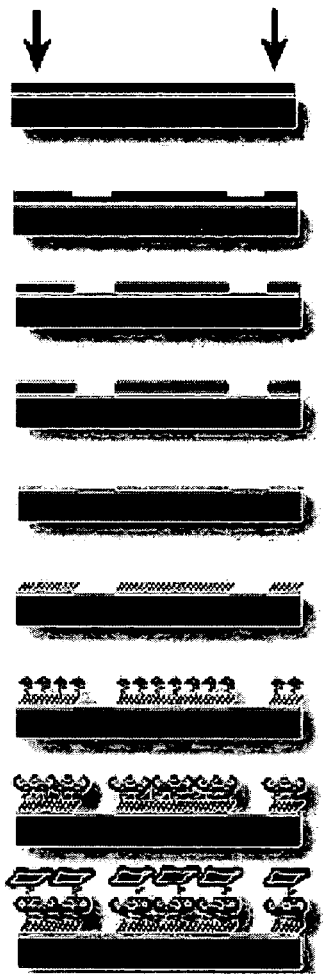
FIG. 1 shows a process flow diagram of substrate patterning and protein immobilization.

The following description of the preferred embodiment(s) is merely exemplary in nature and is in no way intended to limit the invention, its application, or uses.

Selective localization of target molecules, particularly active proteins, to patterns or specific sites is important for development of biosensors, bioMEMS, tissue engineering, and basic proteomic research. The invention provides a flexible technique for selectively patterning target molecules such as bioactive proteins with nanoscale resolution, preferably using nanoimprint lithography and fluoropolymer surface passivation, and more preferably exploiting the specificity of the biotin/streptavidin linkage. This technique achieves high throughput reproducible nanoscale protein patterns with high selectivity and retained biofunctionality, as demonstrated by interactions between patterned antibodies and their antigen. The invention is illustrated using primarily protein as the target molecule.

More specifically, the invention provides a technique for producing high-contrast and high-resolution protein patterns using nanoimprint lithography (NIL) and surface chemical modification. NIL offers the advantages of high throughput, low cost, high reproducibility, and the capability of creating nanopatterns with features as small as 10 nm over large areas. In NIL, a glass Si or other template, fabricated by e-beam lithography or other suitable techniques, is pressed against a polymer-coated substrate heated to above the glass transition temperature of the polymer. After cooling, the template is removed from the substrate, leaving an imprint of the template features in the polymer. In one preferred approach, in order to immobilize proteins, the patterned substrate is then modified sequentially with an aminosilane, biotin, streptavidin, and finally a select biotinylated target protein. The present technique yields nanopatterned proteins that retain their biological functionality, as demonstrated by antigen binding by patterned antibodies. This technique is compatible with protein patterning on both oxidized Si wafers, which may take advantage of the wealth of microfabrication techniques developed by the semiconductor industry for integrating immobilized proteins into bioMEMS devices, and on optical quality coverglass suitable for microscopic analysis of protein distributions and interactions.

Many applications of patterned biomolecules can be enhanced by improving the resolution of the protein features. Smaller feature sizes enable, for example, the fabrication of high-density protein arrays for biosensors or proteomic screening, or facilitate studies of cellular interactions with small precisely located clusters of extracellular matrix proteins. A major advantage of the nanoimprint technique is that the feature size is reducible to the nanoscale to create high-density arrays, or potentially control placement of individual proteins, while still retaining high throughput and reproducibility. The present invention improves on protein patterning using conventional photolithography to form a base template for protein adsorption, limited to micron-scale resolution by the light diffraction limit. Dip-pen lithography and e-beam patterning are capable of attractive resolution, but these are relatively delicate serial processes and thus lack scalability. The NIL of the present invention provides a method of patterning substrates with resolutions down to less than 200 nm, desirably less than 100 nm, more desirably less than 75 nm, most desirably less than 50 nm, and preferably less than 10 nm or sub-10 nm, on the scale of individual protein molecules.

The most important criterion for any target molecule or protein patterning technique is specific binding of target proteins, i.e., the technique must produce a high density of biomolecules in desired regions (patterned regions or binding regions) while preventing adsorption of these molecules in other regions (unpatterned regions or passivated regions). To satisfy this criterion, the present invention selectively passivates a substrate with a base pattern of an inert, nonpolar $(CF_x)_n$ (x=1 or 2, n=number of monomer subunits, monomer MW=31 or 50) polymer coating to establish a template for the selective attachment of target linker molecules for highly specific covalent binding of biotin, which serves as a site for generalized protein binding through strong non-covalent biotin-streptavidin interactions.

Further alternative binding arrangements include surface functionalization that includes agents binding Carboxy-silane instead of amino-silane and using appropriate linkers to link biotin or target protein. There is also the inserting of various lengths of alkyl spacers to alleviate steric hindrances and surface effects. In another aspect, the functional silanes (amino- or carboxy-) are mixed with relatively inert silanes, such as alkyl-, PEG-, or hydroxy-silanes. Mixed silanes may result in greater binding efficiency/surface density in subsequent layers.

In yet further variations of target protein binding, rather than using NHS-biotin—streptavidin linkages, it is possible to directly bind the target molecule to the functionalized surface. This is achieved by, for example, SATA (succinimidyl acetylthioacetate) or SPDP (succinimidyl 3-(2-pyridyldithio)propionate), heterobifunctional crosslinkers, linking amine to thiol groups; Glutaraldehyde, amine-amine crosslinker; and/or EDAC (1-ethyl-3-(3-dimethylaminopropyl)carbodiimide), amine-carboxyl crosslinker.

In another aspect, a photoactivatable biotin is used. A derivative of biotin bearing a photoremovable group that inhibits binding to streptavidin. When exposed to an appropriate dose of light (typically UV), the photoremovable group is cleaved, enabling biotin-streptavidin binding. Example: Pirrung and Huang, *Bioconjugate Chemistry*, Vol. 7(3), pp. 317-321, 1996.

Alternatives to streptavidin are known and include Neutravidin; and "smart" streptavidin: pH-, temperature-, or light-sensitive streptavidin (Hoffman et al, *Journal of Biomedical Materials Research*, Vol. 52(4), pp. 577-586, 2000)

Accordingly, there are several classes of molecules that can be used as protein capture agents. Antibodies are a class of naturally occurring protein molecules that are capable of binding targets with high affinity and specificity. The properties and protocols of using antibody are known. Antigens can also be used as protein capture agents if antibodies are intended targets for detection. Protein/enzyme or their fragments can be used as protein capture agents as well. Nucleic acid ligands can be used as protein capture agent molecules. A variety of other natural and synthetic molecules are known having antibody-binding affinity and specificity.

Biotin is a coenzyme that is covalently attached to several enzymes involved in the transfer of activated carboxyl groups. Biotin labeling of molecules, biotinylated, can be used to label, detect, purify, and/or immobilize such molecules. These methods also rely upon the proteins avidin and streptavidin, which bind very tightly and specifically to biotin and other biotin-binding molecules.

The term "linker" or "linking agent" refers to a molecule or group of molecules (such as a monomer or polymer) that connects two molecules and often serves to place the two molecules in a preferred configuration. As used herein according to one aspect of the invention, a linking agent such as aminosilane links substrate surface oxides to target-molecule-capturing agents such as biotin/streptavidin.

The term "protein" is well known in the art and usually refers to a very large polypeptide, or set of associated polypeptides, that has some biological function. For purposes of the present invention the terms "peptide," "polypeptide," and "protein" are largely interchangeable.

As used herein, "glass" generally refers to a hard, amorphous, inorganic, usually transparent, brittle substance made by fusing silicates, sometimes borates and phosphates, with certain basic oxides and then rapidly cooling to prevent crystallization. As used herein, glass is understood to be a brittle, noncrystalline, usually transparent or translucent material that is generally formed by the fusion of dissolved silica and silicates with soda and lime. Glass is further understood to be any of a large class of materials with highly variable mechanical and optical properties that solidify from the molten state without crystallization, that are typically based on silicon dioxide, boric oxide, aluminum oxide, or phosphorus pentoxide, that are generally transparent or translucent, and that are regarded physically as supercooled liquids that are essentially solids.

Other substrates useable in the invention include a metal or a compound of a metal, preferably comprising at least one of the following: gold, silver, platinum, and indium-tin oxide.

EXAMPLE 1

FIG. 1 schematically illustrates the patterning process. A silicon mold was fabricated by standard e-beam lithography and dry etching. To facilitate mold separation after imprinting the mold was coated with surfactant, perfluorochlorosilane (Lancaster Synthesis, Windham, N.H.) to provide a low energy surface. The material to be imprinted, poly(methyl methacrylate) or PMMA (Aldrich, St. Louis, Mo.) was spun onto a substrate of either 60 nm thick silicon oxide thermally grown on silicon, or onto optical grade glass wafers (Erie Scientific, Portsmouth, N.H.). The PMMA was patterned by NIL: the mold and substrate were brought into physical contact at 175° C., and a pressure of 50 kg/cm$^2$ was applied for 5 min before cooling to room temperature. After the mold and substrate were separated, $O_2$ reactive ion etching (RIE) was used to remove PMMA residual in the patterned regions ($O_2$ gas flow=20 sccm, pressure=20 mTorr, power=50 W) and $CHF_3$ RIE was used to etch the newly exposed oxide ($CHF_3$ gas flow=40 sccm, $O_2$ gas flow=5 sccm, pressure=20 mTorr, power=150 W), transferring the patterns to the oxide layer. In addition to etching away the exposed $SiO_2$ to the underlying Si substrate, this etching process deposits a thin passivating layer of $CF_x$ polymer residue on the newly exposed Si surface. The presence of this passivating polymer residue was verified by X-ray energy dispersive spectroscopy (XEDS). The remaining PMMA was then removed by sonication in acetone, leaving exposed $SiO_2$ regions separated by regions of $CF_x$-passivated Si. Note that it is not necessary to etch down to the Si surface, as evidenced by the success of using the same fabrication procedure on glass substrate. Thus, the same technique is used on glass.

FIG. 1 shows a process flow diagram of substrate patterning and protein immobilization. Spin-coated PMMA polymer is patterned by NIL. Exposed $SiO_2$ regions are etched and a passivating $(CF_x)_n$ polymer (x=1 or 2, n=number of monomer subunits, monomer MW=31 or 50) is deposited during a $CHF_3$ RIE procedure. Residual PMMA is stripped away with acetone, exposing the underlying $SiO_2$ in the "patterned regions." An aminosilane monolayer is covalently attached to the exposed "patterned regions." Biotin-succinimidyl ester is then covalently linked to the primary amine of the aminosilane layer, and streptavidin is bound to the biotin layer. Finally, the biotinylated target protein is bound to the streptavidin layer.

More specifically with reference to FIG. 1, the exposed oxide pattern selectively reacts with an aminosilane to form a covalently bound monolayer. The aminopropyldimethylethoxysilane (APDMES, SIA0603.0, Gelest, Morrisville, Pa.) is particularly effective. The single alkoxy group on the head of this silane ensures the reproducible deposition of a well-formed monolayer by minimizing unwanted self-polymerization. Producing good silane monolayers on exposed silicon oxide or glass requires careful attention to procedure, especially with regards to temperature and humidity. NIL-patterned substrates were heated to 70° C. under dry nitrogen in a 0.4 L glass chamber. A 5 µL portion of APDMES was injected into the chamber through an airtight septum and allowed to react for 20 min with the exposed $SiO_2$ surfaces before venting with fresh nitrogen for 90 s. Samples were then sonicated for 10 min in dry isooctane, followed by ethanol, then 1 mM NaOH to remove unbound silane from the surface and deprotonate the exposed amine. Deprotonation of the amine ensures the monolayer's reactivity to subsequent modifications by nucleophilic substitution reactions. The specificity of the aminosilane deposition was initially quantitatively verified by covalently binding tetramethylrhodamine succinimidyl ester (C-1171, Molecular Probes, Eugene, Oreg.) to the amine tail group of the aminosilane monolayer via an n-hydroxysuccinimide reaction and measuring the resulting fluorescent intensities in the aminosilane patterned regions and the passivated Si regions. A very bright signal was observed in the aminosilane patterned regions, corresponding to a surface density of aminosilane on the order of a monolayer; no detectable fluorescent signal was detected on the passivated regions, indicating the aminosilane does not react with the passivated Si surface. Therefore the plasma deposition of the fluoropolymer layer is responsible for the high differentiation between the two regions.

At this point, the APDMES-functionalized substrate is enclosed in a flow cell, 2.2 cm long by approximately 50 µm deep and 0.5 cm wide, formed by fixing a glass cover slip to the top of 50 µm thick aluminum foil spacers adhered to the substrate with vacuum grease. This allows sequential introduction of various buffers to the substrate, and also allows easy imaging using epifluorescence microscopy. Biotin is covalently bound to the exposed primary amine tail group of the patterned APDMES by filling the flowcell with a 68 µM biotin-succinimidyl ester solution (B-1513, Molecular Probes, Eugene, Oreg.) in 0.1M HEPES buffer at pH 7.65 for 20 min before flushing the flowcell with either deionized water or a biological buffer such as BRB80 (80 mM PIPES, 1 mM $MgCl_2$, 1 mM EGTA, brought to pH 6.8 with KOH). Next a streptavidin layer is deposited and bound to the biotin layer by flushing the flowcell with a 10 µg/mL streptavidin solution in blocking buffer (0.1M HEPES, pH 7, containing 5 mg/mL BSA) and incubating for 15 min. The resultant streptavidin monolayer serves as a base for the specific adsorption of any biotinylated target protein.

Biotinylated BSA served as the initial target protein. The target protein was bound by flushing the flowcell with a 50 μg/mL biotinylated BSA solution in blocking buffer and incubating for 10 min. For fluorescent imaging, the heavily biotinylated BSA was further exposed to a 10 μg/mL rhodamine-labeled streptavidin (S-870, Molecular Probes, Eugene, Oreg.) solution in Blocking Buffer for 10 min. The flowcell was rinsed with 0.1M HEPES, pH 7 containing an oxygen scavenging antifade cocktail (30 mM glucose, 0.6 mg/mL glucose oxidase, 0.12 mg/mL catalase in BRB80) prior to transfer to the microscope stage.

Figure 2:
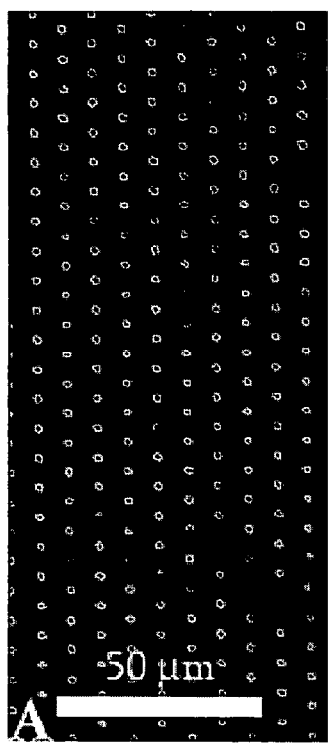
FIG. 2 shows an epi-fluorescence image of rhodamine-labeled streptavidin bound to sharp uniform microscale dots (A) and lines (B) of biotinylated BSA protein on oxidized Si substrates. (C) shows rhodamine-labeled streptavidin bound to patterns of immobilized biotinylated BSA on cover glass.
Figure 2:
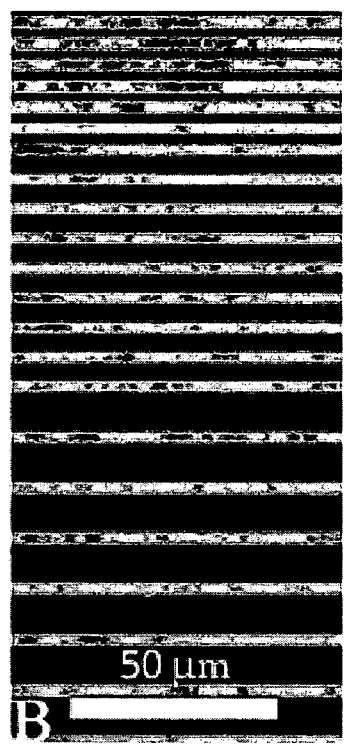
Figure 2:

FIG. 2 shows an epi-fluorescence image of rhodamine-labeled streptavidin bound to sharp uniform microscale dots (A) and lines (B) of biotinylated BSA protein on oxidized Si substrates. Fluorescent intensity signal in the passivated regions is at or below the noise level of the imaging system, indicating the fluorophore concentration in these areas is less than 0.1% of that observed in the patterned regions. (C) Rhodamine-labeled streptavidin bound to patterns of immobilized biotinylated BSA on cover glass.

EXAMPLE 2

The surface density of target protein in the patterned regions is quantified by calibrating the measured fluorescent intensity of immobilized fluorescently labeled proteins to solutions of the same proteins at known concentration. Fluorescent images of patterned target proteins were captured on a Zeiss Axioplan 2 microscope fitted with a CoolSNAPcf CCD camera (Roper Scientific, Trenton, N.J.). The fluorescent intensity per molecule in the plane of focus was derived briefly as follows.

The total fluorescent intensity captured by the camera, $I_C$, imaging a flowcell of known depth is $$I_C = k_{CCD} I_E = k_{CCD} \int_z \int_r q N_F I_I(z) A(z) \phi(z,r) dr\, dz$$

where $k_{CCD}$ is a constant relating the intensity of light incident on the camera's CCD chip to the camera's electrical signal, $I_E$ is the total fluorescent emission captured, q is the quantum efficiency of the fluorophore, $N_F$ is the concentration of fluorophore in solution, $I_I$ is the intensity of the illuminating (excitation) light as a function of chamber depth z, A is the area of the illuminated field of view at depth z, and $\phi$ is the percentage of emitted light from each fluorophore that is captured by the objective lens at depth z and lateral distance r from the center of the image plane.

The illumination $I_I(z)$ can be expressed as $$I_I(z) = I_0 \frac{r_0^2}{(r_0 + z\tan\phi)^2}$$

where $I_0$ is the illumination in the plane of focus, $r_0$ is the illumination spot size in the plane of focus, and $\phi$ is half the angular aperture (NA=n sin $\phi$).

In practice, a flowcell is formed by fixing a glass cover slip to the top of 50 μm thick aluminum foil spacers adhered to the substrate with vacuum grease. A solution of blocking buffer (0.1M HEPES, pH 7, containing 5 mg/mL BSA) is added to the flowcell to saturate the flowcell surfaces to prevent fluorophore from binding nonspecifically. After about one minute, the flowcell is flushed with three flowcell volumes of a solution containing 5 mg/mL BSA and a known concentration of the same fluorophore that was patterned on the sample of interest. The particular concentration of fluorophore varies by sample and is chosen such that when imaged under conditions (illumination intensity, exposure time, etc.) identical to those used when imaging the patterned sample of interest, the measured intensity lies within the dynamic range of the camera. Images of this calibration flowcell are then taken near the upper surface of the chamber immediately after imaging the patterned substrate, as the lamp intensity slowly drifts over time. To subtract the background autofluorescence and camera dark current, another flowcell is fabricated and filled with blocking buffer. This flowcell is imaged similarly to the fluorescent calibration flowcell above. The intensity from this background sample is then subtracted from the intensity measured from the fluorescent calibration flowcell to get the experimental value for $I_C$. Because the imaging conditions and fluorophore used on the sample of interest and fluorescent calibration flowcell are identical, many of the terms in the equation for $I_C$ above can be lumped together, greatly simplifying the computation (e.g., $k_{CCD}$, q, $I_0$, and $\phi$ are the same in all samples). Considering potential errors stemming from geometric estimations (i.e., depth of the flowcell), light source instability, electrical noise, and reflectance of fluorophore emittance off of the $SiO_2$ substrate, we estimate the maximum error in this measurement to be no more than 30%, and insignificant relative to the orders of magnitude difference in specificity achieved.

This analysis shows a surface density of rhodamine-labeled streptavidin in the patterned region of approximately 120 000 molecules/$\mu m^2$, which is on the same order as the surface density expected from a close-packed streptavidin monolayer. Applying this analysis to the passivated Si region, the coverage of target protein in this region is undetectable, giving an upper limit of approximately 50 molecules/$\mu m^2$, or less than 0.1% of a monolayer. This demonstrates nearly complete monolayer coverage of target biomolecule in the patterned regions, with only a negligible amount of target protein adsorbed to the passivated regions.

EXAMPLE 3

Figure 3:
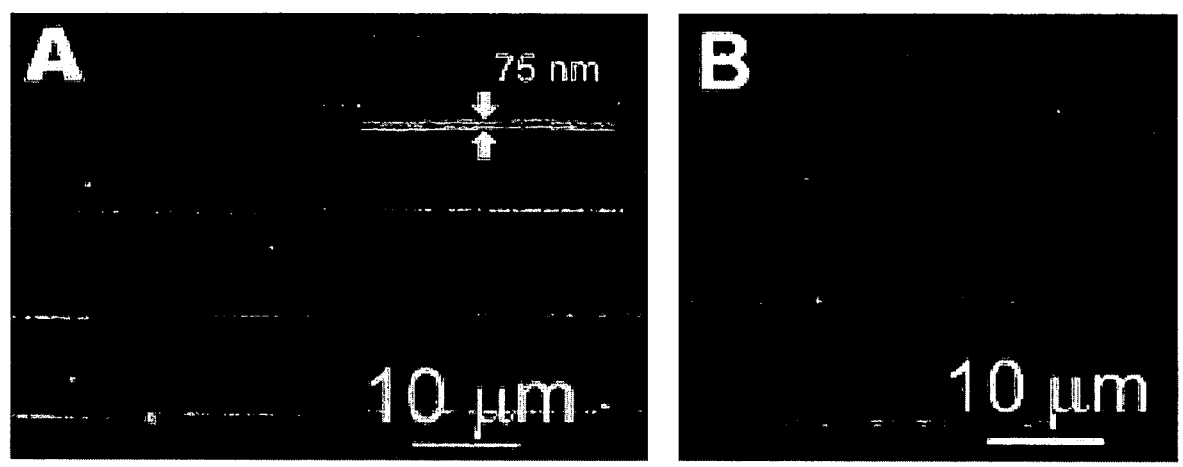
FIG. 3 shows proteins patterned onto sub-100 nm features. (A) SEM image of oxide nanolines formed on a Si substrate by NIL and RIE. (Inset) Close-up SEM of oxide nanoline, showing a line width of less than 100 nm. (B) Fluorescence micrograph of nanolines after patterning with biotinylated BSA and binding rhodamine-labeled streptavidin.

One of the main advantages of using NIL technology in patterning is the ability to achieve resolution in the nanometer scale. Added nanoscale protein patterns were prepared by fabricating a mold to create 75 nm wide lines on Si substrates (FIG. 3). These nanopatterned substrates were prepared identically to the microscale substrates, with biotinylated BSA as the target protein and rhodamine-labeled streptavidin subsequently bound for fluorescent imaging. The surface density measured by fluorescence is consistent with that observed on the micropatterned substrates, indicating an approximate monolayer of adsorbed target protein on the nanolines.

FIG. 3 shows proteins patterned onto sub-100 nm features. (A) SEM image of oxide nanolines formed on a Si substrate by NIL and RIE. (Inset) Close-up SEM of oxide nanoline, showing a line width of less than 100 nm. (B) Fluorescence micrograph of nanolines after patterning with biotinylated BSA and binding rhodamine-labeled streptavidin. Analysis of the fluorescent intensity along the line indicates an approximate monolayer of target protein.

EXAMPLE 4

Broadly useful patterning technology requires that immobilized proteins retain their biological functionality. Here it is demonstrated that the functionality of patterned antibodies is retained by patterning the target protein goat anticatalase (ab6572, Novus Biologicals, Littleton, Colo.) and observing its binding of fluorescently labeled catalase from solution. Substrates were prepared as described above up to the streptavidin layer. A 10 μg/mL solution of biotinylated anticatalase in blocking buffer was then introduced into the flowcell for 10 min. The flowcell was flushed with HEPES pH 7.0, and a 50 μg/mL solution of rhodamine-labeled catalase in blocking buffer was introduced. This solution was incubated 10 min before rinsing with 0.1M HEPES pH 7.0 containing antifade. Fluorescent images show that the labeled catalase binds to the immobilized anticatalase in the patterned regions (FIG. 4), while only a negligible amount binds in unpatterned regions. Quantifying the fluorescent intensity of the bound catalase as explained above yields a surface density of approximately 31 000 catalase molecules/$\mu m^2$, again on the order of a monolayer. This technique is also used to create ultrahigh density antibody arrays for applications such as compact sensors and diagnostic devices, and for proteomic screening. The ability to specifically place small numbers of protein molecules at desired locations also benefits biophysical and molecular biology studies, as well as integration of protein activities into microscale devices (e.g., bioMEMS). Thus, the invention provides binding region target yield at least 10 times greater than other regions, desirably 100 times greater, and more desirably at least 1,000 times greater. Further, the target-molecule-capturing agent has a density of at least 1,000 molecules per square nanometer, desirably at least 10,000 molecules per square nanometer, more desirably at least 50,000 molecules per square nanometer, and most desirably at least 100,000 molecules per square nanometer.

Figure 4:
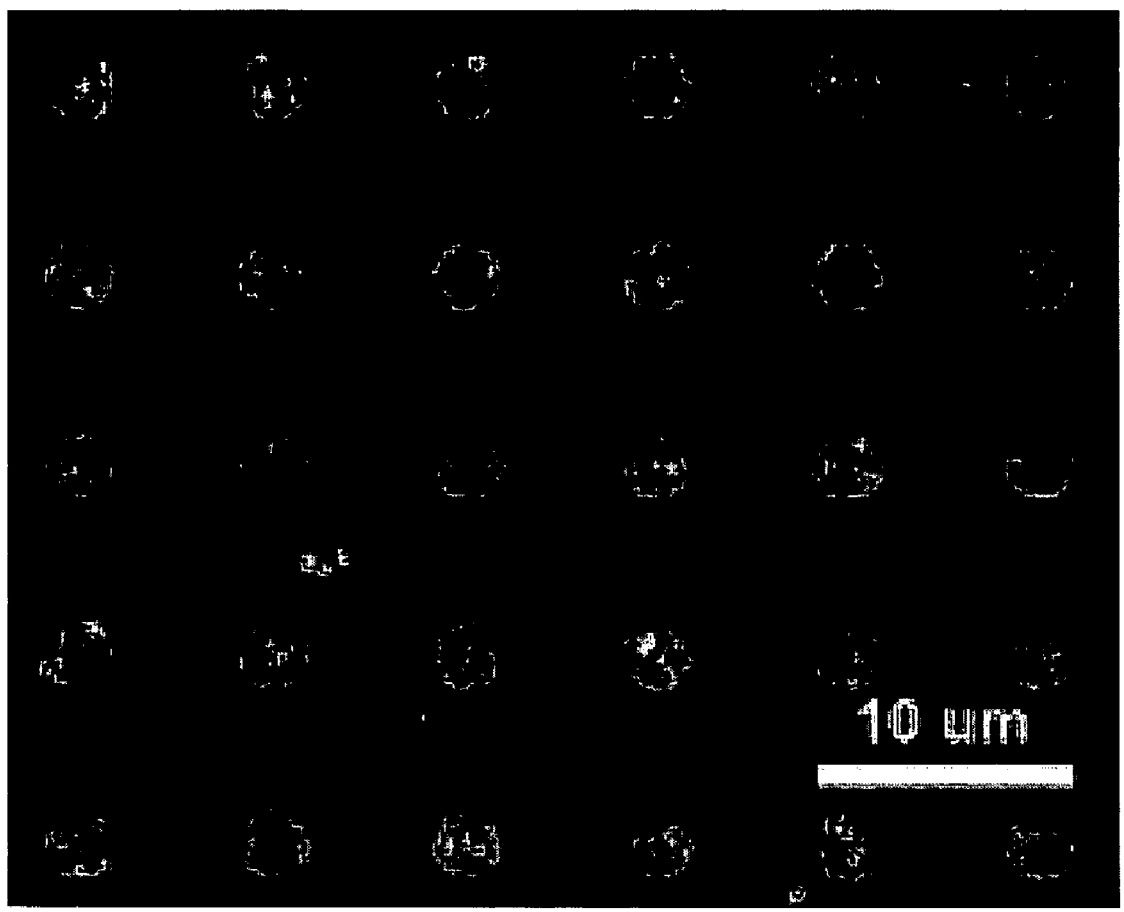
FIG. 4 shows an epi-fluorescence image demonstrating the retained biological activity of patterned biomolecules. Biotinylated polyclonal anticatalase antibody was patterned in 2 µm dots. Here, fluorescent catalase is bound to immobilized anticatalase.

FIG. 4 shows an epi-fluorescence image demonstrating the retained biological activity of patterned biomolecules. Biotinylated polyclonal anticatalase antibody was patterned in 2 μm dots, and the antibody's fluorescent antigen, rhodamine-labeled catalase, selectively binds to the antibody-patterned regions. The surface density of the bound catalase is approximately 31 000 molecules/$\mu m^2$.

In summary, the invention provides a solid support for the attachment of target-molecule-capturing agents, such as protein capture agents. The substrate has regions of chemical functionality for the immobilization of protein capture agents, and other substrate regions that essentially do not bind proteins. These other areas on the substrate surface are essentially without immobilized protein capture agents and target proteins.

The invention provides a technique for immobilizing biomolecules with nanoscale resolution in a process that preserves functionality of the immobilized proteins. The use of nanoimprinting as the patterning method for the initial template enables high throughput ultrahigh resolution patterning. Advantageously, the method uses high affinity biotin-streptavidin binding, and can be applied to pattern virtually any protein, without the high degree of variability expected when protein is immobilized by virtue of more general chemical properties (i.e., hydrophobicity or charge). The target molecules or proteins bind specifically to the ligand patterns, and the nonspecific adsorption is at least 1000-fold lower in the region of the passivation layer. The invention demonstrates feature sizes down to 75 nm, and nanoimprinting achieves features as small as 10 nm across. Thus, placement of individual biomolecules is possible. The compatibility of this technique with both $SiO_2$ substrates as well as optical quality cover glass broadens the potential applications of immobilized proteins, allowing easy integration with MEMS technologies as well as ready access to a wide range of optical imaging, measurement, and manipulation methods. Examples include phase contrast microscopy, differential interference contrast (DIC) microscopy, confocal microscopy, transmission near-field scanning microscopy, and optical trapping.

This versatile, highly specific, and biologically friendly technique for generating ultrahigh resolution protein patterns leads to the integration of diverse activities of proteins into microfabricated devices and sensors. For example, protein chips, arrayed with a myriad of proteins, are becoming a useful tool in proteomics, enabling quick parallel screening of potential protein-protein interactions in large protein populations; as well as in more focused diagnostic biosensors, concentrated on analysis of enzymatic interactions within a smaller set of proteins. Patterning of multiple proteins on a single substrate is encompassed by the invention due to its high contrast and resolution. Thus, the invention provides substrates or chips with protein feature densities more than an order of magnitude greater than those currently available, improving sensitivity, reducing required analyte volumes, and increasing the number of proteins that can be screened against on a single chip.

The invention addresses the need for a method that rapidly and specifically isolates microgram or multi-microgram amounts of proteins and other molecules per square centimeter of surface from a sample, for isolation and characterization of protein.

The invention addresses the need for materials that serve as a matrix or a support for the attachment of protein capture agents. The invention provides a substrate having binding regions with chemical functionality for the immobilization of protein capture agents, and other regions that essentially do not bind proteins being essentially without immobilized protein capture agents.

Importantly, the invention addresses the problem that proteins tend to bind to surfaces in a non-specific manner and, in doing so, tend to lose their biological activity. The invention provides a protein microarray substrate having surface functionality capable of interacting with protein capture agents, resists non-specific protein binding to areas where no protein capture agents have been deposited, and prevents or at least minimizes loss of protein biologic activity. It is recognized that the biological activity of non-specifically bound (NSB) proteins may be irrelevant. Where there is non-specific binding, it is preferable that these non-specifically bound proteins are inactive. However, the substrate is chosen such that it resists non-specific binding, and does not inhibit the activity of specifically bound proteins. It is usually desirable that non-specifically bound proteins lose their biologic activity, while specifically bound proteins retain activity.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for forming a substrate for immobilizing target molecules comprising:
   providing a substrate;
   patterning a film on the substrate by imprint lithography to define first regions and second regions;
   removing the film in the first regions by reactive ion etching (RIE) to provide exposed first regions;
   passivating the exposed first regions to form non-functionalized surfaces;

removing the film in the second regions to provide exposed second regions; and functionalizing the exposed second regions to provide immobilized target-molecule-capturing functionality.

2. The method of claim 1, wherein the immobilized target-molecule-capturing functionality comprises a first functionality bound to the substrate and a second functionality for binding to the target molecule.

3. The method of claim 2, wherein the first functionality comprises an oxy for binding to surface oxide of the substrate, and the second functionality comprises an amine for binding to biotin.

4. The method of claim 3, wherein the second functionality further includes the biotin bound to streptavidin, where the amine is proximal to the substrate and the streptavidin is distal to the substrate.

5. The method of claim 2, wherein the first functionality is bound to the substrate by vapor deposition of a precursor.

6. The method of claim 1, wherein the immobilized target-molecule-capturing functionality comprises a first molecule bound to the substrate by vapor deposition.

7. The method of claim 6, wherein the first molecule is bound to a second molecule, where the second molecule either directly binds the target molecule or indirectly captures the target molecule.

8. The method of claim 1, wherein the passivating is conducted during the RIE by depositing a passivating polymer film from a precursor that decomposes during the RIE.

9. The method of claim 2, wherein the first functionality comprises aminosilane deposited by vapor deposition and the second functionality comprises biotin and streptavidin.

10. The method of claim 9, wherein the biotin and streptavidin are not deposited by vapor deposition.

* * * * *